(12) United States Patent
Roh

(10) Patent No.: US 11,776,698 B2
(45) Date of Patent: *Oct. 3, 2023

(54) VIRTUAL TELEMEDICINE MECHANISM

(71) Applicant: IX Innovation LLC, Seattle, WA (US)

(72) Inventor: Jeffrey Roh, Seattle, WA (US)

(73) Assignee: IX Innovation LLC, Seattle, WA (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/523,708

(22) Filed: Nov. 10, 2021

(65) Prior Publication Data

US 2022/0139568 A1    May 5, 2022

Related U.S. Application Data

(63) Continuation of application No. 17/228,384, filed on Apr. 12, 2021, now Pat. No. 11,200,987.

(60) Provisional application No. 63/008,302, filed on Apr. 10, 2020.

(51) Int. Cl.
```
G08B 1/08      (2006.01)
G16H 50/80     (2018.01)
G16H 40/67     (2018.01)
G16H 80/00     (2018.01)
A61B 5/00      (2006.01)
G16H 50/30     (2018.01)
G16H 50/20     (2018.01)
```

(52) U.S. Cl.
CPC ........... *G16H 50/80* (2018.01); *A61B 5/0022* (2013.01); *A61B 5/6801* (2013.01); *A61B 5/746* (2013.01); *G16H 40/67* (2018.01); *G16H 50/20* (2018.01); *G16H 50/30* (2018.01); *G16H 80/00* (2018.01)

(58) Field of Classification Search
CPC ........ G16H 50/80; G16H 40/67; G16H 50/20; G16H 50/30; G16H 80/00; G16H 10/20; G16H 10/40; G16H 10/60; G16H 20/00; G16H 30/20; G16H 40/20; G16H 40/63; G16H 50/70; A61B 5/0022; A61B 5/6801; A61B 5/746
USPC .... 340/539.12, 539.13, 539.11, 686.1, 539.1
See application file for complete search history.

(56) References Cited

U.S. PATENT DOCUMENTS

| | | | | |
|---|---|---|---|---|
| 11,200,987 B2 * | 12/2021 | Roh | ................. | G16H 10/60 |
| 2012/0253831 A1 * | 10/2012 | John | ................. | G06Q 40/00 |
| | | | | 705/2 |
| 2014/0039911 A1 * | 2/2014 | Iyer | ................. | G06Q 30/0207 |
| | | | | 705/2 |
| 2017/0039338 A1 * | 2/2017 | Khindaria | ............ | G16H 70/20 |
| 2018/0047120 A1 * | 2/2018 | Mathis | ................. | G06Q 50/22 |

* cited by examiner

*Primary Examiner* — Anh V La
(74) *Attorney, Agent, or Firm* — Perkins Coie LLP

(57) ABSTRACT

Systems and methods related to virtual telemedicine systems, virtual examinations, medical marketplaces, and/or assistance for patient/physicians are provided. The systems can be configured to identify relevant medical service providers based on user-specific information, whether the user has experienced a medical event that may require emergency, urgent, or non-urgent medical services, and/or provide examinations, such as virtual examinations, in person examinations, or hybrid examinations (e.g., both a virtual examination with a first physician and a physical examination with another physician).

20 Claims, 7 Drawing Sheets

VIRTUAL TELEMEDICINE MECHANISM

CROSS-REFERENCE TO RELATED APPLICATIONS

This application is a continuation of U.S. patent application Ser. No. 17/228,384, filed Apr. 12, 2021 (now U.S. Pat. No. 11,200,987), which claims the benefit of U.S. Provisional Patent Application No. 63/008,302, filed Apr. 10, 2020, both of which are incorporated herein by reference in their entireties. This application contains subject matter related to U.S. Provisional Application No. 62/538,051 and U.S. application Ser. No. 16/049,751; the related applications are hereby incorporated by reference in their entireties.

TECHNICAL FIELD

The present technology is directed generally to virtual telemedicine systems and technology for assisting user and/or physicians, and more particularly related to virtual technologies for conducting virtual examinations and supporting medical providers.

BACKGROUND

Various conditions or circumstances may prevent a patient from obtaining in-person physical examinations. For example, a patient may not have a sufficient mode of transportation and/or the required travel distance may not be reasonable due to one or more patient conditions/circumstances. Also, in-person visit may present unreasonable and/or avoidable risks, such as due to the patient health condition or community-wide epidemics. To further complicate the issue, different geographic locations (e.g., countries, states, counties, etc.) may have varied health care facilities, which may present challenges for non-native patients (e.g., visitors or recent transplants) seeking suitable medical assistance. In some situations, local medical facilities and/or the corresponding personnel may not be equipped with have desired or required expertise, medical equipment, and/or other resources. Thus, there is a need for a telemedicine system for providing virtual examinations and for assisting users, physicians, and health care providers.

BRIEF DESCRIPTION OF THE DRAWINGS

The accompanying drawings illustrate various embodiments of systems, methods, and embodiments of various other aspects of the technology. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1:
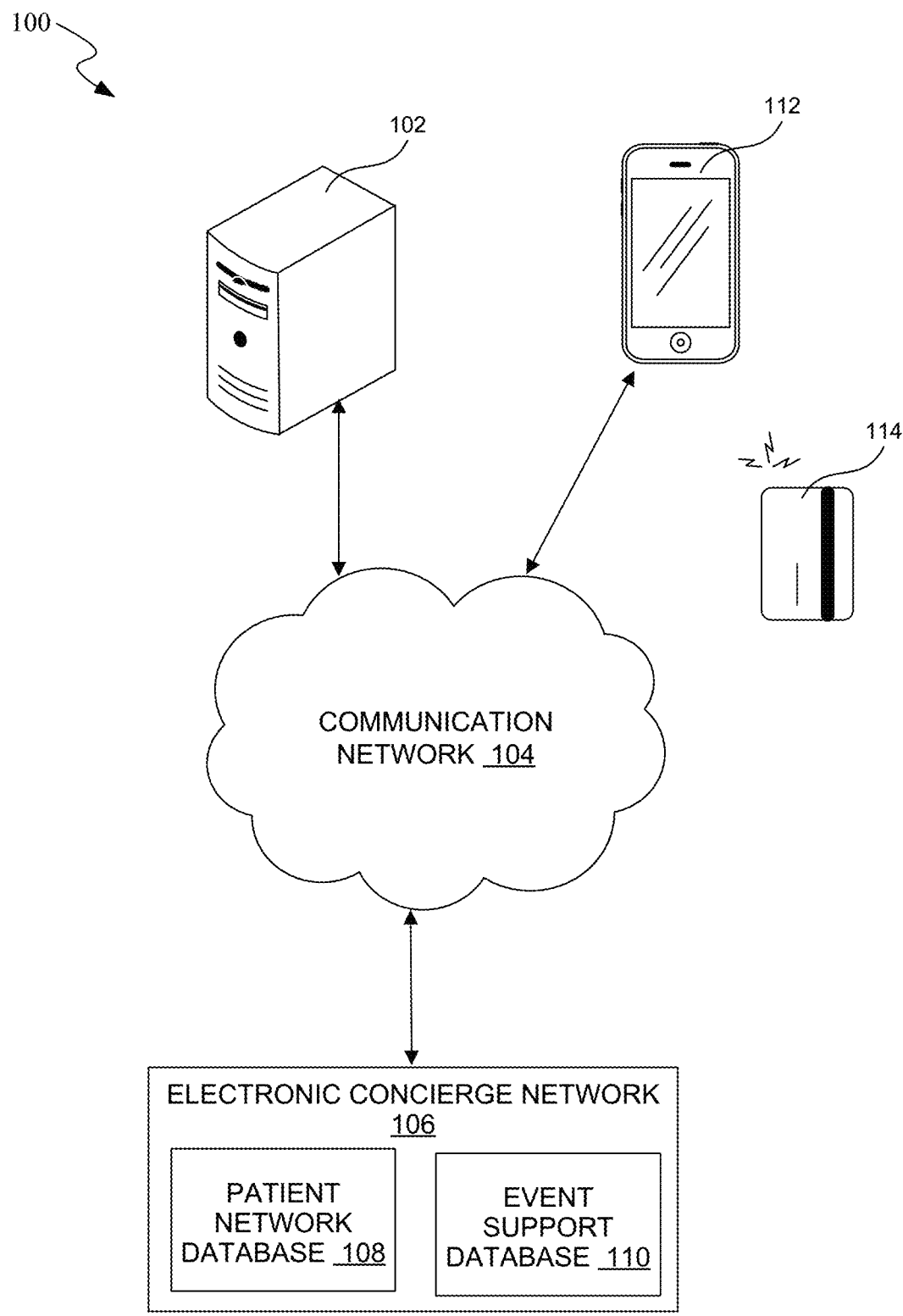
FIG. 1 illustrates an example network connection in association with a virtual telemedicine mechanism in accordance with one or more embodiments of the present technology.

Systems and methods related to virtual telemedicine mechanism (e.g., a circuit, a device, a software, a firmware, or a combination thereof), such as for providing virtual examinations and/or for assisting patient and/or physicians is described below. The technology described herein may be configured to identify relevant medical service providers and/or provide medical services (e.g., examinations) based on user-specific information. For example, the virtual telemedicine mechanism can assist the user experiencing a medical event that may require emergency, urgent, or non-urgent medical services. The virtual telemedicine mechanism can be configured to conduct or assist with virtual medical care, in person medical care, or hybrid medical care (e.g., allowing both in-person and remote medical personnel to service a patient).

In one aspect, a method of providing assistance to a user (e.g., a patient, a healthcare professional, or the like) in discovering medical services may be provided. The method can include providing one or more databases storing user data and support network data. The user data can include one or more of user personal data, user medical data, and user preference data. The user can be identified based on at least one of a unique identity code or biometric details. Relevant local and/or remote providers can be identified. For location-based recommendations, the method can further include receiving event data associated with the user and determining a geographical location of the user. Relevant support network data can be identified based on the event data and the geographical location of the user. The relevant local support network data can be presented for viewing by the user. For non-geographic based recommendations, the method can further include receiving data provided by the user, and relevant support network data can be presented to the user.

The support network data may include information regarding healthcare providers located throughout the world. The user data can be provided to a health-care provider prior, during, and/or after an examination. The system can analyze the user data to support examination, diagnosis, and/or treatment.

In another aspect, a method can include receiving user identifier data, user data (e.g., electronic medical records, test data, etc.), and event data provided by a user. A user can be identified based on the user identifier data and reference user data associated with the user. The method can further include receiving geographical location data associated with the user. Relevant support network data, marketplace data (e.g., medical resources available to the user) can be identified based on the event data and the geographical location data. The relevant support network data can be transmitted for viewing by the user. In some embodiments, the relevant support network data can be configured to be displayed on a map with at least one of the event data or the user preference data. In some embodiments, the relevant support data can be displayed along with virtual examination capabilities for various healthcare providers. This allows the user to select healthcare providers capable of conducting virtual services (e.g., virtual clinic sessions, virtual examinations, etc.) based on telemedicine data, such as devices (e.g., smart phones, tablets, computers, cameras, video cameras, imaging systems, etc.) available to the user. The system can identify virtual services available to the user based upon the telemedicine data. For example, if the user has access to an imaging system or video cameras, the system can indicate whether a physician is able to generate a 3D image, hologram, or other three-dimensional or two-dimensional representation of the user for conducting one or more virtual examinations.

In another aspect, a system can include one or more databases storing user details and support network data. The user details can include user personal data, user medical data, and user preference data, and the support network data can include data of individuals and agencies providing medical support. The system can further include one or more processors, and memory. The memory can comprise instructions that, when executed by the one or more processors, cause the system to identify the user based on matching of at least one of a unique identity code and biometric details with the user details. In some embodiments, the system can receive event data provided by the user and obtain geographical location data associated with the user. Relevant support network data can be identified based on the event data and the geographical location data. In some embodiments, the system can receive telemedicine information from the user and relevant support network data can be identified based on the telemedicine information. The system can provide relevant support network data to the user.

In another aspect, a non-transitory computer-readable storage medium is provided. The non-transitory computer-readable medium can store instructions that, when executed by a computing system, cause the computing system to perform a method for discovering medical services or medical services (1) within a designated area or region, (2) supporting telemedicine, (3) associated with a virtual medical marketplace, or (4) combinations thereof. The method can include receiving user details and support network data. The user details can include user personal data, user medical data, and user preference data, and the support network data can include data of individuals and agencies providing medical support. The user can be identified based on matching of at least one of a unique identity code and biometric details with the user details. In some embodiments, the method can further include receiving event data provided by the user and receiving a geographical location of the user. Relevant support network data can be identified based on the relevant data and the geographical location of the user. The relevant support network data can be provided to the user as a map overlaid with at least one of the event data and the user preference data. In some embodiments, the method can further include receiving telemedicine data provided by the user and can identify the relevant support network based on the received data. The system can provide software, apps, or other resources supporting telemedicine functionality. For example, the user can download one or more applications for communicating with a physician. The applications can support voice calls, video communications, or the like.

An example application of the virtual telemedicine mechanism can be for diagnosing and/or treating COVID-19 or similar infectious diseases. The global COVID-19 pandemic has deeply touched and adversely impacted virtually every community in ways that are difficult to comprehend. Unlike other common seasonal illnesses, the indelible effect of the current COVID-19 public health crisis may be with us for many generations to come. While many countries in Asia have had a more recent experience with similar viral outbreaks such as SARS, MERS, and H1N1, many other communities have not experienced a pandemic of this magnitude since the Spanish Flu of 1918. Due to the more recent exposures and the resulting lessons, Asian countries may have been better prepared to respond to the COVID-19 pandemic, such as by bolstering the inventory of necessary products and services, implementing recently-learned best practices (e.g., early and frequent comprehensive diagnostic testing). The present technology can be used as a response to such contagious/pandemic events and avail medical examinations and remedies while reducing occasions for disease transmissions. Moreover, the present technology may enable patients and/or medical professionals and entities to access and leverage health-care services across the world, including in better-equipped or more recently-relevant geographic locations.

To combat COVID-19 or similar infectious diseases, the virtual telemedicine mechanism may provide and/or connect users to Comprehensive Monitoring Systems. Accordingly, the virtual telemedicine mechanism may expand access to diagnostic tests by efficiently connecting the mismatch in supply and demand for tests. Effectively, the virtual telemedicine mechanism can facilitate a marketplace to connect the supply and demand of products and services, including diagnostic RT-PCR and antibody/antigen tests. The virtual telemedicine mechanism can also increase transparency in both the price and quality of diagnostic tests in the marketplace. Accordingly, the virtual telemedicine mechanism can protect against price gouging and provide quality controls and quality assurance programs.

In addition to facilitating the care and the marketplace, the virtual telemedicine mechanism can provide identification of active infections for comprehensive monitoring and provide virtual patient monitoring via a cloud-based, digital platform for quarantine management. Effectively, the virtual telemedicine mechanism can establish evidence-based criteria to provide guidelines for safe and effective quarantine and de-quarantine management, as well as for redeployment of first responders, nursing home staff, and healthcare providers back to the work force.

In the following, numerous specific details are set forth to provide a thorough understanding of the present technology. In other embodiments, the techniques introduced here can be practiced without these specific details. In other instances, well-known features, such as specific functions or routines, are not described in detail in order to avoid unnecessarily obscuring the present technology. References in this description to "an embodiment," "one embodiment," or the like mean that a particular feature, structure, material, or characteristic being described is included in at least one embodiment of the present technology. Thus, the appearances of such phrases in this specification do not necessarily all refer to the same embodiment. On the other hand, such references are not necessarily mutually exclusive either. Furthermore, the particular features, structures, materials, or characteristics can be combined in any suitable manner in one or more embodiments.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Many embodiments or aspects of the present technology described below can take the form of computer- or controller-executable instructions, including routines executed by a programmable computer or controller. Those skilled in the relevant art will appreciate that the described techniques can be practiced on computer or controller systems other than those shown and described below. The techniques described herein can be embodied in a special-purpose computer or data processor that is specifically programmed, configured, or constructed to execute one or more of the computer-executable instructions described below. Accordingly, the terms "computer" and "controller" as generally used herein refer to any data processor and can include Internet appliances and handheld devices (including palm-top computers, wearable computers, cellular or mobile phones, multi-processor systems, processor-based or programmable consumer electronics, network computers, mini computers, and the like). Information handled by these computers and controllers can be presented at any suitable display medium, including a liquid crystal display (LCD). Instructions for executing computer- or controller-executable tasks can be stored in or on any suitable computer-readable medium, including hardware, firmware, or a combination of hardware and firmware. Instructions can be contained in any suitable memory device, including, for example, a flash drive, USB device, and/or other suitable medium, including a tangible, non-transient computer-readable medium.

The terms "coupled" and "connected," along with their derivatives, can be used herein to describe structural relationships between components. It should be understood that these terms are not intended as synonyms for each other. Rather, in particular embodiments, "connected" can be used to indicate that two or more elements are in direct contact with each other. Unless otherwise made apparent in the context, the term "coupled" can be used to indicate that two or more elements are in either direct or indirect (with other intervening elements between them) contact with each other, or that the two or more elements co-operate or interact with each other (e.g., as in a cause-and-effect relationship, such as for signal transmission/reception or for function calls), or both.

The following embodiments are described in sufficient detail to enable those skilled in the art to make and use the invention. It is to be understood that other embodiments would be evident based on the present technology, and that system, process, or mechanical changes may be made without departing from the scope of an embodiment of the present invention.

FIG. 1 illustrates an example network connection 100 in association with a virtual telemedicine mechanism (e.g., a set of circuits and/or software configured to provide healthcare services through remote/mobile devices) in accordance with one or more embodiments of the present technology. The virtual telemedicine mechanism can correspond to one or more systems and/or methods for supporting medical services. The virtual telemedicine mechanism can identify relevant medical service providers based on user-specific information (e.g., user identity, geographical location, user preferences, user resources, etc.) and event data (e.g., real-time information indicating that the user has experienced a medical event that may require emergency, urgent, or non-urgent medical services). For example, the system can automatically determine a set of medical service providers customized to the user's particular location, preferences, and medical condition, and visually present that set to the user in an easily understandable format, such as an overlay map on the user's smart phone, list of available telemedicine services, etc.

The virtual telemedicine mechanism can include a system 102 (e.g., one or more computing devices, such as a server, a personal computer, etc.) connected with a communication network 104. The communication network 104 may further be connected with an electronic concierge network 106 for allowing data transfer between the system 102 and the electronic concierge network 106. Optionally, the communication network 104 may further be connected with a user device 112 (e.g., a personal device, such as a mobile computing device, a smart phone, a wearable device, a continuous health monitor, etc.) for allowing data transfer between the user device 112, the system 102, and/or the electronic concierge network 106.

The system 102 can be configured to provide real-time medical information to a user. For example, the system 102 can include hardware circuitry and/or software configured to assist the user discover medical services across different geographic locations (e.g., local, remote, such as different cities, states, and/or countries). Also, the system 102 can enable the user to interact in real-time with other participants, such as for providing medical services.

The communication network 104 may be a wired and/or a wireless network. Any wireless portions of the communication network 104 may be implemented using communication techniques such as Visible Light Communication (VLC), Worldwide Interoperability for Microwave Access (WiMAX), Long Term Evolution (LTE™), Wireless Local Area Network (WLAN), Infrared (IR) communication, Public Switched Telephone Network (PSTN), Radio waves, and other communication techniques known in the art.

The electronic concierge network 106 can include a set of devices (e.g., hardware circuits and/or software) configured to facilitate medical services in real-time using or interfacing with devices in multiple remote locations. For example, the electronic concierge network 106 can include a support system for identifying nearby services, supporting virtual services, and/or providing a marketplace for medical resources.

In one embodiment, the electronic concierge network 106 may be implemented via a cloud network. The electronic concierge network 106 may include a patient network database 108 and/or an event support database 110. The patient network database 108 may be configured to store patient data, such as personal data, user medical data, and/or user preference data. The stored data can include, without limitation, patient records, medical data (e.g., medical history, familial medical history, allergies, medications), billing information, insurance information, employer information, preference data (e.g., preferred doctors and/or facilities), travel itinerary, risk score (e.g., contagious disease score), or the like. The patient network database 108 may further include outputs or results (e.g., device-monitored health data and/or user-reported data) provided by the user device 112. The event support database 110 may be configured to store support network data representative of persons and places that provide medical services, such as pharmacies, doctors, hospitals, clinics, third parties, insurance, and/or payment agents. The event support database 110 may store a user Identity (ID) of the user, biometric data, user profiles (e.g., telemedicine data), and/or authentication data and may store the data along with a current geographical location of the user.

The user device 112 may include a device having suitable software and hardware components for receiving input data from a user and for displaying output data to the user. The user device 112 may include an output display. Alternatively or additionally, the user device 112 may couple to a display to provide the output data. In one embodiment, relevant information may be displayed on a Graphical User Interface (GUI). A smart phone is shown as an example of the user device 112 in FIG. 1. Further, the user device 112 may be any other device including a GUI, for example, a laptop, desktop, tablet, phablet, mobile device, or other such devices known in the art. The user device 112 may include a local software application (e.g., a desktop application, web application, or mobile application) configured to implement the various methods described herein and may include one or more imaging devices, including cameras. The user device 112 may further include a wearable device, a continuous health monitoring circuitry (e.g., a blood glucose monitor, a heart rate monitor, etc.). The user device 112 may be configured to communicate directly with the system 102 (via, e.g., a peer-to-peer communication or a direct link), or indirectly via the communication network 104.

In some embodiments, the virtual telemedicine mechanism can include a user identifier 114. The user identifier 114 can include a device, a structure, a software, a biometric signature or a representation thereof, or a combination thereof configured to uniquely identify the user. For example, the user identifier 114 can include a card configured to provide a unique code or identifier (via, e.g., Near Field Communication) representative of the user. In other embodiments, the user device 112 can include a biometric sensor configured to detect a physiological feature (e.g., a finger print) of the user as the user identifier 114.

For illustrative purposes, an example configuration for the present technology is depicted in FIG. 1. However, it is understood that alternative configurations may be used. For example, the user device 112 may include or be combined with the system 102 or one or more components thereof. Accordingly, some or all of the functionality described herein with respect to the system 102 may also be performed by the user device 112, and vice-versa. Moreover, the system 102 may include or be combined with the electronic concierge network 106 or one or more components thereof (e.g., the patient network database 108 and/or the event support database 110). Accordingly, some or all of the functionality described herein with respect to the system 102 may also be performed by the electronic concierge network 106, and vice-versa.

Figure 2:
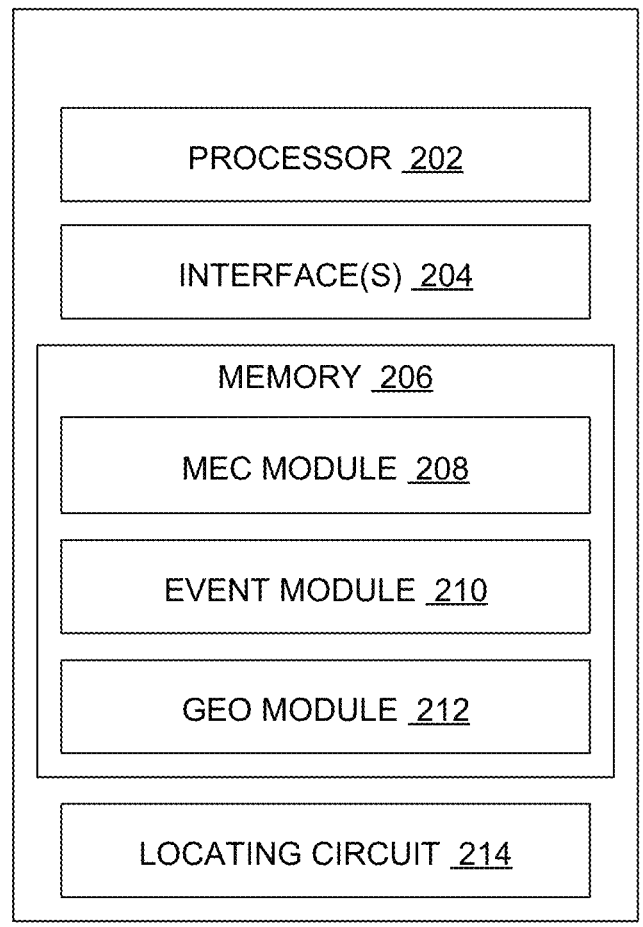
FIG. 2 illustrates a block diagram for the virtual telemedicine mechanism in accordance with one or more embodiments of the present technology.

FIG. 2 illustrates a block diagram for the virtual telemedicine mechanism in accordance with one or more embodiments of the present technology. The virtual telemedicine mechanism can include (at, e.g., the system 102 of FIG. 1, the user device 112 of FIG. 1, one or more devices in the electronic concierge network 106, or a combination thereof) one or more processors 202, one or more interfaces 204 and/or memory 206.

The processors 202 can include data processors (e.g., central processing units (CPUs), graphics processing units (GPUs), System On Chip (SOC) devices, special-purpose computers, and/or onboard servers) configured to execute instructions (e.g., software instructions) stored on one or more portions of the memory 206. The processors 202 can implement the program instructions to control/interface with other devices, thereby causing the virtual telemedicine mechanism to execute actions, tasks, and/or operations. The processor 202 may execute an algorithm stored in the memory 206, thereby providing real-time assistance to the user in discovering and supporting medical services. The processor 202 may also be configured to decode and execute any instructions received from one or more other electronic devices or server(s).

The interfaces 204 can be configured to couple different circuits and/or devices to each other. For example, internal interfaces can include a bus, such as a system bus, a Peripheral Component Interconnect (PCI) bus or PCI-Express bus, a HyperTransport or industry standard architecture (ISA) bus, a small computer system interface (SCSI) bus, a universal serial bus (USB), an IIC (I2C) bus, or an Institute of Electrical and Electronics Engineers (IEEE) standard 1394 bus (also referred to as "Firewire"). Examples of external interfaces can include communication circuits and/or network interfaces configured to facilitate device-to-device communications. The interfaces 204 can further include user interfaces configured to provide an interface between the user and one or more devices of the virtual telemedicine mechanism. The user interface can accept an input from the user and/or provide an output to the user. The interface(s) 204 may either be a Command Line Interface (CLI), Graphical User Interface (GUI), or a voice interface. In some embodiments, the GUIs can include a dashboard for providing data to the user, such as in managing virtual clinic sessions.

The memory 206 may include, but is not limited to, fixed (hard) drives, magnetic storage mediums, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions and/or data.

The memory 206 may include modules (e.g., instruction groupings and/or functions) executable by the processor 202. In one case, the memory 206 may include a Mobile Electronic Concierge (MEC) module 208, an event module 210, and a geo module 212. The memory 206 can be non-transitory computer-readable storage medium storing instructions that, when executed by a computing system, cause the computing system to perform methods disclosed herein. The MEC module 208 can be configured to provide the concierge functionalities. For example, the MEC module 208 can enable the electronic concierge network to perform one or more functions described below. Also, the MEC module 208 can enable the system 102 and/or the user device 112 to interface with the electronic concierge network 106. The event module 210 can be configured to facilitate real-time determination of a user context. For example, the event module 210 can be configured to detect real-time user conditions, such as health-related emergencies, using the event support database 110, the system 102, and/or the user device 112. Also, the event module 210 can provide an interface between the event support database 110, the system 102, and/or the user device 112. The geo module 212 can be configured to determine a current location of the user, such as by determining a current location of the user device 112. The geo module 212 can include instructions for interacting with a locating circuit 214 to determine the current location, such as based on triangulation-based derivations and/or dead-reckoning derivations. Some examples of the locating circuit can include a Global Positioning System (GPS) device or receiver, a motion sensor (e.g., an accelerometer and/or a compass), a motion tracker, a radio signal detector (e.g., a node-specific reference signal detector for WIFI/Cell triangulation derivations), or the like.

Figure 3:
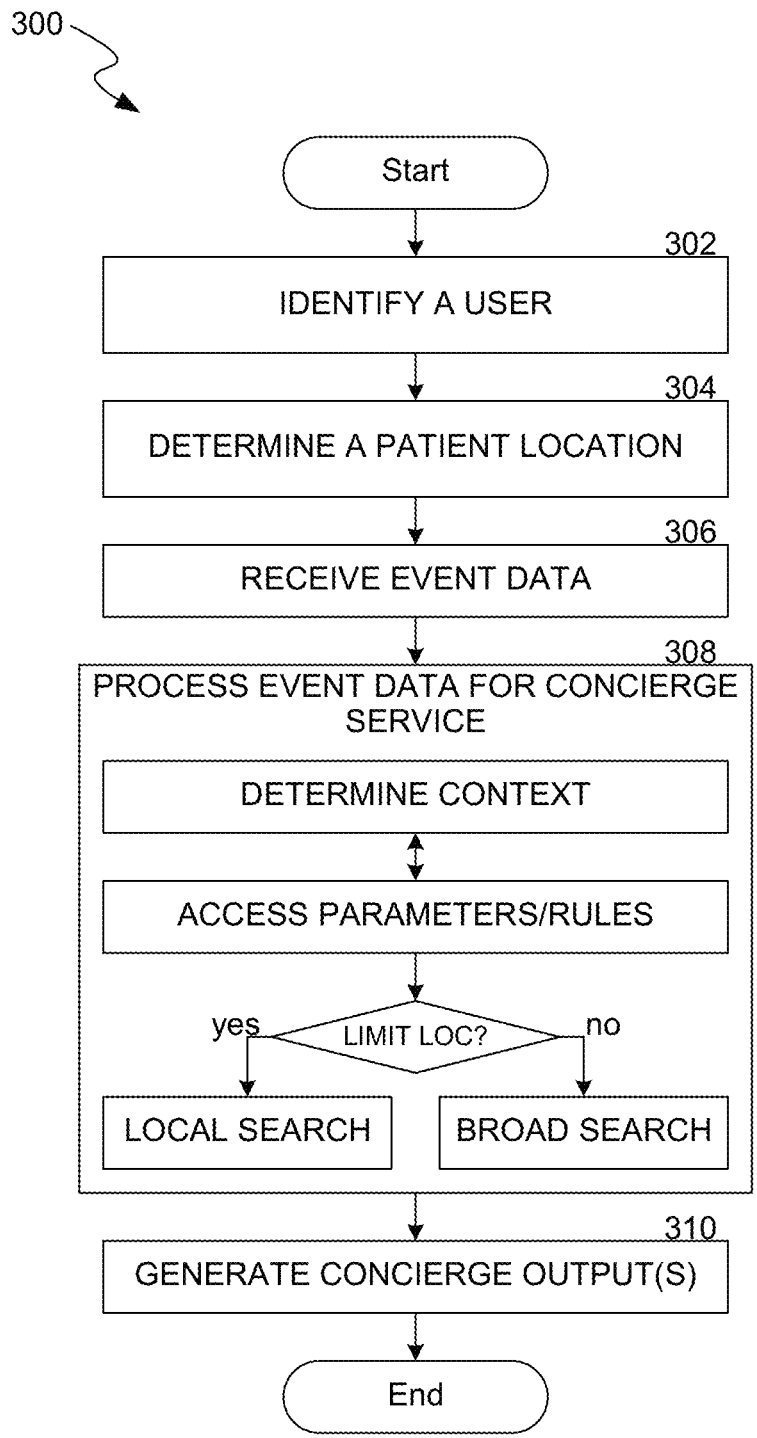
FIG. 3 illustrates a flow diagram for a first example method of operating the virtual telemedicine mechanism in accordance with one or more embodiments of the present technology.

FIG. 3 illustrates a flow diagram for a first example method 300 of operating the virtual telemedicine mechanism in accordance with one or more embodiments of the present technology. The method 300 can be for providing real-time concierge service to a user/patient. For example, the method 300 can be for locating medical resources (e.g., equipment, tests, services, etc.) according to a current context of the patient. The method 300 can be implemented by the system 102 of FIG. 1, the user device 112 of FIG. 1, the electronic concierge network 106 of FIG. 1, the MEC module 208 of FIG. 2, and/or the event module 210 of FIG. 2.

One skilled in the art will appreciate that, for this and other processes and methods disclosed herein, the functions performed in the processes and methods may be implemented in differing order. Furthermore, the outlined steps and operations are provided as examples, and some of the steps and operations may be optional, combined into fewer steps and operations, or expanded into additional steps and operations without detracting from the essence of the disclosed technology.

At block 302, the virtual telemedicine mechanism can identifier a user (e.g., a patient) accessing the concierge service. For example, the user device 112 and/or the system 102 can receive an input, such as a user-identifier and password, data from or representative of the user identifier 114, etc., uniquely associated with the user. The user device 112 can compare the input to a predetermined list or data associated with one or more authorized users. Also, the user device 112 can provide the identification input to the system 102 and/or the electronic concierge network 106 for authentication.

The user may be identified/authenticated based on matching of at least one of a unique identity code or biometric details with reference user data, also referred to herein as user details. In one embodiment, the user is identified based on both a unique identity code and biometric details. For example, the system 102 may receive the unique identity code and/or biometric details from the user, and can compare the unique identity code and/or biometric details with previously stored user data or details (e.g., user details previously stored in one or more databases of the electronic concierge network 106) or reference user data. If the unique identity code and/or biometric details match the stored user details, the user is successfully identified, and the system 102 can proceed to step 304.

At block 304, the virtual telemedicine mechanism can determine the geographical location of the user. For example, in response to successfully authenticating the user, the user device 112 can use the locating circuit 214 and/or the geo module 212 to derive the current location (e.g., GPS coordinates) of the user device 112. The user device 112 can interact with other devices or systems (e.g., satellites, transmitters, location servers, etc.) to derive the current location in real-time. The user device 112 can implement a predetermined process, such as GPS-based derivations, triangulation, or dead-reckoning navigation, to derive the current location. The current location of the user device 112 may be provided to other devices, such as the system 102, the electronic concierge network 106, a map server, for further processing. Alternatively or additionally, the virtual telemedicine mechanism may predict a future location of the user. The predicted future location can be determined in a variety of ways, such as using a user-provided travel itinerary data that includes times and locations of travel. The user may input a particular time at which medical services are desired (e.g., a future date for refilling a prescription). The user device 112 and/or system 102 can compare the input time with the travel itinerary data to determine the predicted future geographical location of the user during that time.

At block 306, the virtual telemedicine mechanism can receive event data representative of the patient/user condition. For example, the system 102 and/or the electronic concierge network 106 can receive health-related data and/or context-related data from the user device 112. The user device 112 can provide user-input information, data from wearable devices, outputs from continuous health monitors through the communication network 104 of FIG. 1. In some embodiments, the user device 112 can continuously stream the health-related data and/or the context-related data, and the system 102 and/or the electronic concierge network 106 can analyze the received data to determine a medical event (e.g., a medical emergency). Additionally or alternatively, the user device 112 can compare the health-related data and/or the context-related data to a set of predetermined template values to determine a triggering event (e.g., a recognizably dangerous heartbeat pattern, a threshold blood sugar level, etc.). Based on the triggering event, the user device 112 can alert the system 102 and/or the electronic concierge network 106 of the determined event and/or provide the relevant data.

In some embodiments, the user device 112 can locally detect emergencies (e.g., life-threatening events) according to a set of predetermined thresholds/templates and notify the system 102 and/or the electronic concierge network 106 accordingly. As an illustrative example, the virtual telemedicine mechanism can determine a heartrate threshold and/or a noteworthy heartbeat pattern appropriate for the past medical history and/or current condition of the user. The virtual telemedicine mechanism can compare the data from the wearable heartrate monitor to determine whether or not the user is experiencing a heart attack or other heart-related health events. Alternatively or additionally, the user device 112 can interact with the system 102 and/or the electronic concierge network 106 for detecting one or more predetermined events.

The event data may be received in the form of, but not limited to, a text string, or an audio request, or an audio request reduced to a text string, or an image. For example, the user input can include an image of a wound, audio (e.g., audio of a user requesting services), image data for generating an image representing of the user, and/or text describing the services requested. Further, the event data may include a set of questions to be answered by the user (e.g., questions regarding the type, timing, and/or severity of symptoms), and/or the user's responses thereto. The event data can be answers to one or more questions for determining user health, condition information, pain information, allergy information, and priority information. The priority information can be used to determine whether or not the user requires immediate assistance, urgent care, transportation, isolation (e.g., due to a contagious disease), or the like. If processing the event module 210 determines that the user requires immediate attention, medical assistance can be sent to the user. If executing the event module 210 determines that urgent care should be provided, the event module 210 can identify at least one available urgent care facility. The Mobile Electronic Concierge (MEC) module 208 can receive and store the event data from the user and/or event module 210.

At block 308, the virtual telemedicine mechanism can process the event data for providing concierge service. For example, the system 102 and/or the electronic concierge network 106 can analyze the received data according to information in the patient network database 108, such as past and/or current health conditions of the user, to identify user context. The virtual telemedicine mechanism can access records associated with medical emergencies (e.g., heart attack, severe injury, fainting, allergic reactions), preventative visits, examinations, prescription records, non-emergency care, or the like. The virtual telemedicine mechanism can further access family history of the user, the travel itinerary, risk scores and/or current health-related status (e.g., circulating diseases, pollution level, weather forecast, etc.). The virtual telemedicine mechanism can use the accessed information to determine a set of applicable templates, thresholds, and/or rules. The virtual telemedicine mechanism can compare the event data to the determined set of templates/thresholds to identify a user context and/or for inputs controlling subsequent services related to the identified context.

As an illustrative example, the virtual telemedicine mechanism can access the symptoms and/or related measurement patterns indicative of diseases occurring within a threshold distance from the current location of the user. The virtual telemedicine mechanism can compare the received event data to the accessed symptoms or associated data patterns to determine whether or not the patient user is experiencing the same symptoms and/or a likelihood that the user has been infected with a corresponding disease.

In response to the event/context recognition, the virtual telemedicine mechanism can perform a search for heath resources (e.g., specialists, medical facilities, medical equipment, etc.) according to a set of predetermined parameters and/or rules associated with the identified user context. The virtual telemedicine mechanism may perform a location-based search when the identified context matches a set of location-limited events (e.g., refilling prescription) and/or time sensitive events (e.g., life-threatening emergencies). In performing the location-based search, the virtual telemedicine mechanism can use additionally derived results, such as an estimated travel time in comparison to a predetermined window for the determined health event, to process the search results.

For other types of user context, the virtual telemedicine mechanism can perform a search for targets at other remote locations. For such search, the virtual telemedicine mechanism can account for expertise or recent experiences of the medical service providers with the identified user context. For example, the virtual telemedicine mechanism can rank healthcare providers in certain Asian countries higher than other locations for COVID-related events and/or score the doctors/facilities according to the date of last service associated with the user context. When the search results are outside of a home country of the user, the virtual telemedicine mechanism can account for medical staff language proficiency and/or accessibility for translation services for the user-preferred language in processing the result. Moreover, the search results can account for availability of the matching healthcare resources, such as due to differences in time zones. The virtual telemedicine mechanism can similarly perform a search for user-requested health resources.

In some embodiments, the virtual telemedicine mechanism can process the event data based on crowd-sourced data (via, e.g., machine-learning and/or artificial intelligence mechanisms). The virtual telemedicine mechanism can process user-provided health data and/or previous feedback/usage from other users to provide the concierge service. For example, the virtual telemedicine mechanism can score searched results (e.g., services, personnel, or other like medical resources) according to frequency of use, review indications, recovery results, subsequent health conditions, etc. associated with previous users having the same user context. Also, the virtual telemedicine mechanism can provide higher weights to search results that match previous search results and/or corresponding responses for other users matching contexts, histories, and/or health data matching those of the current user. Accordingly, the user selection or response to the concierge service can be included into the learning/training data for subsequent events/services. In one or more embodiments, the virtual telemedicine mechanism can infer similar personalities or preferences with other users based on matches in non-health-related information. Such similarities can further be used to derive weights in providing the search results.

At block 310, the virtual telemedicine mechanism can generate concierge output(s) based on the analysis. For example, the virtual telemedicine mechanism can output or display the search results, facilitate virtual examination sessions, and/or provide relevant data (e.g., current health-related data, previous medical records, etc.) to selected medical facility/personnel, etc.

Figure 4:
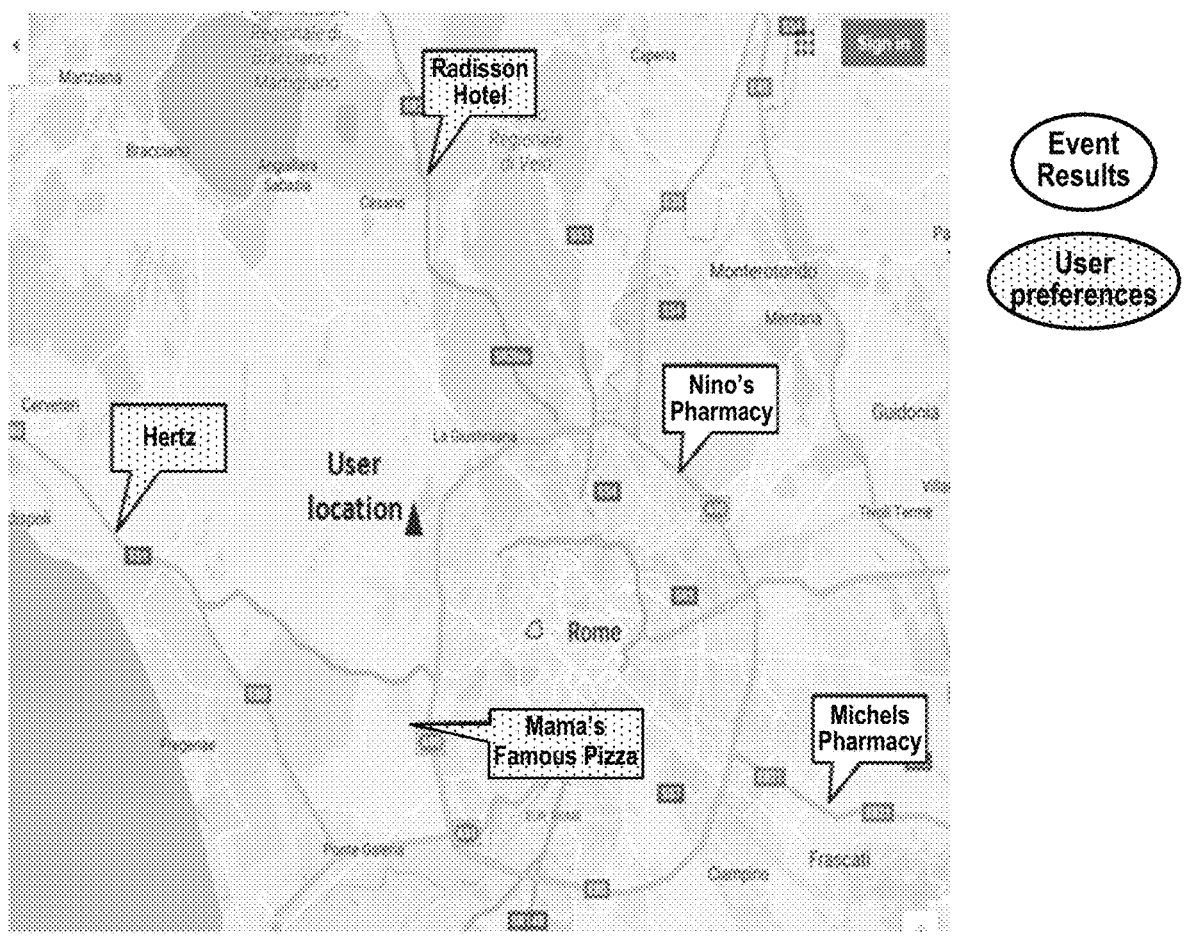
FIG. 4 illustrates a first example concierge output in accordance with one or more embodiments of the present technology.

FIG. 4 illustrates a first example concierge output in accordance with one or more embodiments of the present technology. In some embodiments, the first example concierge output may be presented as a map overlaid with the event data and/or the user preference data, as illustrated in FIG. 4. Further, the event data and/or the user preference data may be filtered and shown based on the current geographical location of the user. The relevant support network data may include locations and information related to medical service providers, such as pharmacies, doctors, hospitals, clinics, third parties, insurance, payment agents, and the like. Such locations and information may be filtered based on the current geographical location of the user and may be presented to the user in form of the relevant support network data. For example, locations may be excluded based on estimated travel time, traffic conditions, availability of transportation (e.g., buses, trains, etc.), or the like. The user can adjust the filter settings.

The illustrated example can correspond to a non-emergency and/or location-limited search result. For example, the virtual telemedicine mechanism can provide pharmacy recommendations based on the user current location and previously visited locations, such as a booked hotel, a rental car service, and the like. The virtual telemedicine mechanism can use the distances between the current location and/or previously-visited locations to derive a feasible travel distance. The virtual telemedicine mechanism can limit the search results to locations within the feasible travel distance from the current location.

Figure 5:
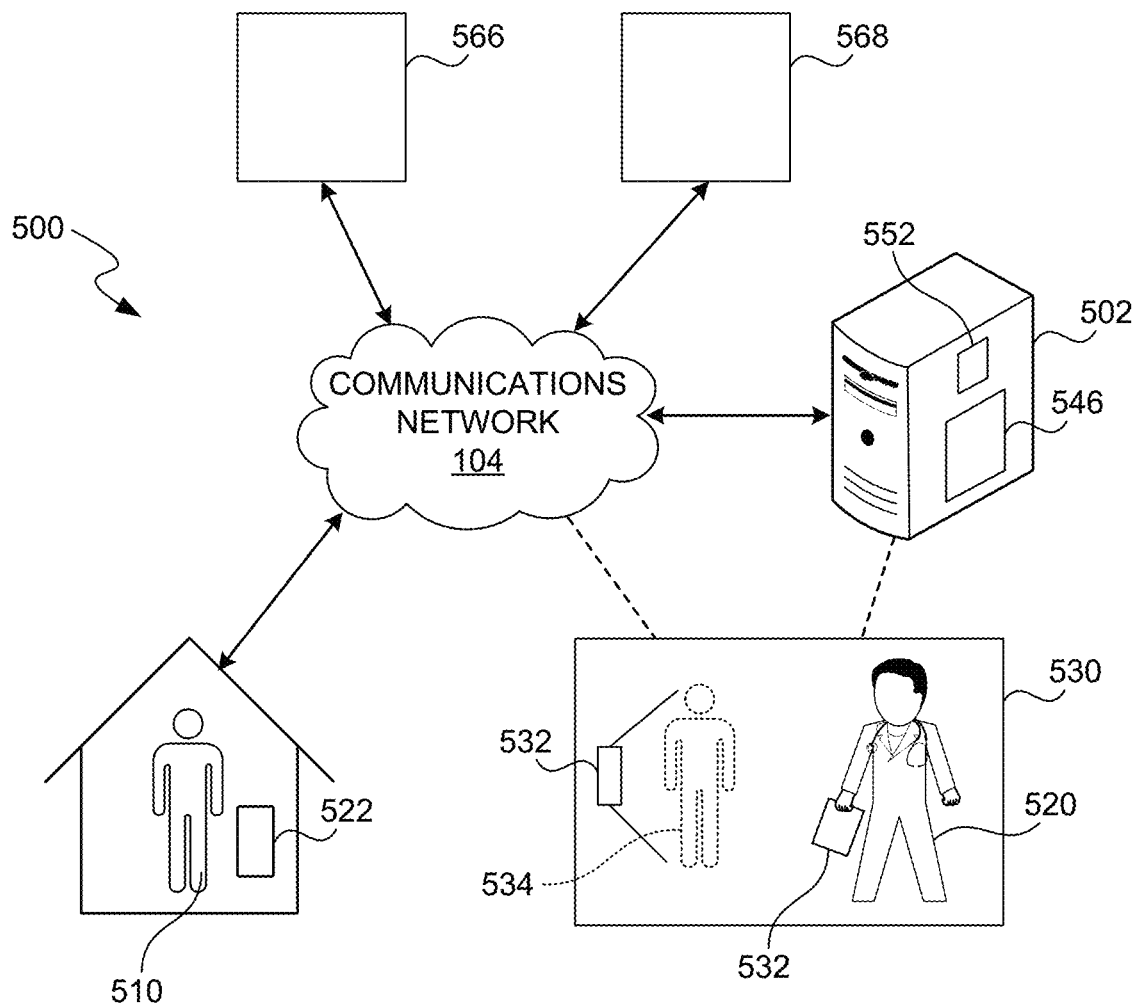
FIG. 5 illustrates an example treatment assistance system in accordance with one or more embodiments of the present technology.

FIG. 5 illustrates an example treatment assistance system 500 in accordance with one or more embodiments of the present technology. The example treatment assistance system 500 can correspond to a second example concierge output for notifying relevant support network for the determined event.

The virtual telemedicine mechanism can identify the relevant support network data as the search results (e.g., facilities, medical personnel, and/or other medical resources) corresponding to the event data, user preference data, the current and/or predicted future geographical location of the user, etc. as described above. The relevant support network data may include locations and information related to medical service providers, such as pharmacies, doctors, hospitals, clinics, third parties, insurance, payment agents, and the like. In some embodiments, the system 102 of FIG. 1 can use the event data, user preference data, and/or the current and/or predicted future geographical location of the user to automatically identify a subset of medical service providers (e.g., a subset of the providers from the support network data stored in event support database 110 of FIG. 1) that are relevant to the identified context (e.g., are suitable for responding to the current event, fulfill some or all of the preferences, and/or are located within a predetermined distance from a current or predicted future geographical location). In some embodiments, the relevant support network data may include telemedicine providers.

As an illustrative example, the event module 210 of FIG. 2 can be executed (via, e.g., the processors 202 of FIG. 2) to evaluate the event data and determine that the user has, for example, a time-critical emergency that may require surgery. The MEC module 208 of FIG. 2 can determine a relevant support network data that includes a medical facility capable of providing surgical services. In another case, the event module 210 may evaluate the event data and determine that the user has non-urgent infection. The MEC module 208 and/or concierge network can then determine a relevant support network data that includes a clinic and a pharmacy. The user can select a recommended pharmacy near a hotel, place or work, or home to conveniently purchase medication. If the user is travelling, the MEC module 208 and/or concierge network can identify relevant support network data based on the user's itinerary, which can be retrieved from the mobile device (e.g., device 112) or inputted by the user. For example, if the user is travelling to another city, the relevant support network data can include a pharmacy near the user's hotel in that city. The relevant support network data can therefore provide a medical services plan for the user's trip. In another embodiment, the relevant support network data can include different sets of relevant support network data. For example, a first set of relevant support network data for discovering medical services near a user's residence and a second set of relevant support network data for discovering medical services near the user's place of work. The relevant support network data can include information about the services, such as hours of operation, ratings, directions to/from medical facilities. In response to a pandemic, the event module 210 can automatically send alerts, notifications, and other data to the user, as well as information about telemedicine services and virtual marketplaces.

The virtual telemedicine mechanism can further provide services to users that are healthcare professionals. For example, the system 102 and/or the electronic concierge network 106 can screen or filter patients to match the capacity, specialty, and/or the capability of the service provider, thereby eliminating wasted resources caused by mismatches. Also, the system 102 and/or the electronic concierge network 106 can facilitate virtual examinations using one or more video conferencing tools. Moreover, the system 102 and/or the electronic concierge network 106 can provide the healthcare provider with the patient information, even when the patient is incapacitated or speaks a different language.

As an illustrative example, FIG. 5 illustrates the treatment assistance system 500 (e.g., an implementation of the network connection 100 of FIG. 1) for providing virtual care to a patient user. In other words, the treatment assistance system 500 can correspond to a subsection of the network connection 100 facilitating real-time medical services with patients and healthcare providers at different locations.

The treatment assistance system 500 can communicatively couple a patient 510 located at a patient site 518 (e.g., residence, hotel room, etc.) with a physician 520 located at a physician site 530 (e.g., hospital, office, clinic, residence, etc.). At the patient site 518, an image capture system 522 (e.g., the user device 112 of a patient-user) can capture image data of the patient 510 or a portion of patient's body. The captured data can be communicated through the communication network 104 and provided at the physician site 530, where an imaging system 532 (e.g., the user device 112 of a physician-user) can generate a virtual patient image 534 (shown in dashed line) based on the received data. Also, the virtual telemedicine mechanism can similarly reproduce captured data (e.g., images, voice signals, text, etc.) from or of the physician 520 and communicate it to the patient 510. The virtual telemedicine mechanism can also communicate the patient data (e.g., the current location, health records, current data from wearable devices or monitoring applications, personal information, etc.) to the physician 520. In some embodiments, the system 522 and/or the system 532 can provide augmented reality (AR) imaging, virtual reality (VR) imaging, 3D imaging (e.g., 3D HD), or combinations thereof for the real-time interactions. The rendered image can provide an immersive viewing experience similar to physical examinations. Also, the physician and/or the patient may be able to pinpoint locations on the body of the communicating party or the recipient body to assist in the communication. For example, the treatment assistance system 500 can overlay or project instructive images and/or the physician movements to the body of the patient user in guiding the recipient user (e.g., the patient or someone near the patient) to perform physician guided actions (e.g., data gathering stimulus or first-aid measures).

The treatment assistance system 502 can include at least one database 552 and module 546. The database 552 can be configured to store reference data, such as historical and/or clinical data from the same patient, other patients (e.g., groups of prior patients), simulation data, data from practice databases, data obtain by research institutions, clinical trials, or the like. The module 546 can be configured with one or more algorithms for providing clinical decision support, analyzing patient data, diagnosis, generating protocols (e.g., diagnostic protocols, testing protocols, evaluation protocols, etc.), generating treatment plans, or the like. The treatment assistance system 502 can provide certainty ratings, treatment risk data, predicted outcomes, predicted related follow-up treatments, or the like. In some embodiments, the treatment assistance system 502 can continuously or periodically analyze data to determine near real-time or real-time data. In some embodiments, the module 546 can assist with diagnosis and treatment based on one or more known factors. The factors can include, without limitation demographic information (e.g., age, gender, etc.), patient complaints (e.g., chief complaints, complaint history), history of present illness, medical data, past medical history, past surgical history, medications, allergies, social history, review of systems, vitals, height, weight, BMI, physical exam findings, lab results, diagnostic tests, imaging results, or the like. Based on the factors and the pattern of diagnosis, treatment, and known outcome measures, the module 546 can generate recommendations regarding products/services that are available via the marketplace, generate a treatment plan, and provide recommendations (e.g., product recommendations based on reviews such as physician reviews, patient outcomes, etc.).

The module 546 can be configured with one or more algorithms to generate at least one of diagnostic support using clinical knowledge, statistics, machine learning, AI, neural networks, or the like. In some embodiments, one or more algorithms are used to identify correlations between data sets, patient parameters, healthcare provider parameters, healthcare resource parameters, treatment procedures, medical device designs, marketplace parameters, and/or treatment outcomes. The data sets can include, without limitation, physician-specific datasets, patient-specific datasets, aggregated datasets, healthcare provider datasets, best standard practice datasets, datasets generated using simulations, or the like. One or more correlations can be used to develop at least one predictive model that generates diagnosis score, predicts the likelihood that a diagnosis is accurate, treatment plan provides a favorable outcome, or the like. The model(s) can be validated, e.g., by inputting data into the model(s) and comparing the output of the model to the expected output. Algorithms can also be applied to improve display and viewing of the virtual patient image 534 based on, for example, physician settings, preferences, or the like.

The module 546 can use one or more AI techniques to develop computing systems capable of simulating aspects of human intelligence, e.g., learning, reasoning, planning, problem solving, decision making, etc. AI techniques can include, but are not limited to, rule-based systems, case-based reasoning, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the module 546 can generate output using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data (e.g., reference diagnostic data, patient data, etc.) stored in database 552, such as a plurality of reference provider data sets or a selected subset thereof (e.g., a plurality of similar patient data sets, physician data sets, etc.). The output can be a diagnosis based on historical patient data. In some embodiments, the module 546 can be trained with physician specific machine learning models. For example, machine learning can be initially performed for each physician based on physician specific training datasets. This allows the module 546 to provide recommendations consistent with a physician's preferences, habits, patterns, etc. The module 546 can optionally adjust the specific train models based on best practices, healthcare provider data, aggregate data sets (groups of physician data set), or the like. In other embodiments, the module 546 can be trained using a non-physician specific training dataset. The module 546 can be further trained using physician specific and/or non-specific data. This allows for training flexibility.

In some embodiments, the machine learning model, such as a neural network or a naïve Bayes classifier, may be trained on the training data set using a supervised learning method, such as a gradient descent or stochastic gradient descent. The training dataset can include pairs of generated "input vectors" with the associated corresponding "answer vector." The model can be run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate an examination plan, a diagnosis, and/or treatment plan, a data set can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether a diagnosis is accurate, various candidate treatment procedures and/or medical device designs are likely to produce a favorable outcome for the patient, etc. Based on these calculations, the trained machine learning model(s) can select at least one examination plan, diagnosis, and/or treatment plan. In embodiments where multiple trained machine learning models are used, the models can be run sequentially or concurrently to compare outcomes and can be periodically updated using training data sets. The module 546 can use one or more of the machine learning models based the model's predicted accuracy score. In some embodiments, the trained machine learning model(s) can adaptively provide real-time output based in physician and/or user input. The trained machine learning model(s) can determine or select one or more questions, requests for information, and other output for conducting the examination, diagnosis, etc. In some embodiments, the trained machine learning model(s) can select procedures based on, for example, reimbursement (e.g., whether procedures qualify for reimbursement, such as governmental reimbursement, insurance reimbursement, etc.), regulations (e.g., governmental regulations, FDA regulations, etc.), patient preferences (e.g., length of treatment, cost limits, etc.), or the like.

The treatment assistance system 502 can include one or more components of the system 102 discussed in connection with FIGS. 1 and 2. In some embodiments, the treatment assistance system 502 can provide concierge services for identifying, selecting, scheduling a virtual clinic session. The treatment assistance system 502 can provide the portal, applications, or other technology for conducting telemedicine services. The system 500 can include the system 102 discussed in connection with FIG. 1 so that the system 500 is capable of discovering medical services and supporting medical services, as well as available medical sources for purchase or lease. Recommendations can be reviewed by the physician who can assist the patient in selecting, for example, local medical services near the patient, telemedicine services, virtual services, or the like. This can reduce the time to treatment, enable examinations (e.g., enable examinations of quarantined or remote patients), etc.

The system 500 can provide a virtual medical marketplace for selling, leasing, and/or purchasing medical equipment and supplies. Sellers 566, 568 can list products via a cloud-based marketplace via the communication network 504. The system can match sellers and buyers based on geographic data (e.g., buyers and sellers within a preset distance), transport criteria, price, regulatory schemes, or the like. In pandemic settings (e.g., contagious virus setting), the marketplace can be used to acquire a scarce supply of resources (e.g., personal protective equipment, respirators, ventilators, etc.) and provide users with price information (e.g., patient price transparency) via a GPS-based system. The module 546 can apply one or more algorithms to match buyers and sellers to facilitate health-care provider decisions. If the module 546 predicts there will be shortage of resources, the module 546 can select recommend products and sellers, provide resource predictions, and preparation protocols for providers to limit or avoid a shortage of resources that could impact patient care. Predictive forecasting can be provided to manufacturers, regulatory agencies, and/or suppliers to manage manufacturing, pricing, distribution, or the like.

Figure 6:
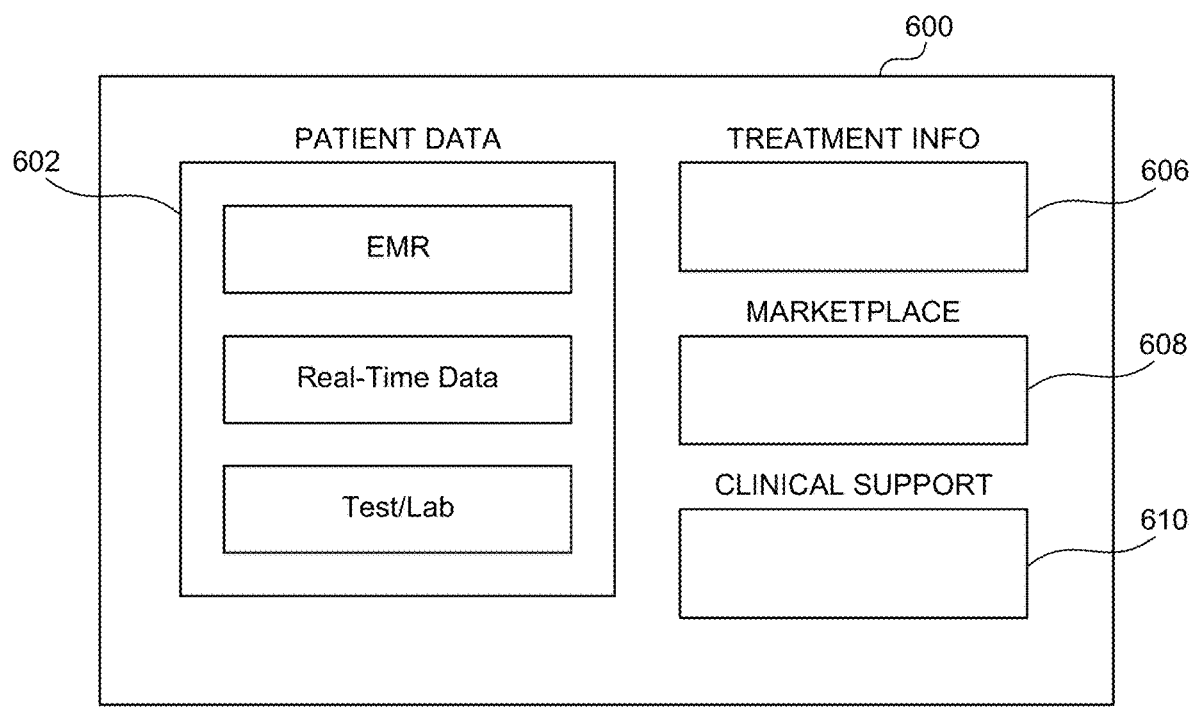
FIG. 6 is an example dashboard in accordance with one or more embodiments of the present technology.

FIG. 6 is an example dashboard 600 in accordance with one or more embodiments of the present technology. The dashboard 600 can include or display patient data 602, treatment information 606, marketplace 608, and clinical support 610. The patient data 602 can include one or more electronic medical records, real-time data (e.g., wearable obtained data), test data, lab data, patient preferences, physician notes, patient feedback (e.g., feedback acquired via questionnaires), data from wearables (e.g., heart rate data, exercise data, etc.), test data, imaging data (e.g., camera images, MRI images, ultrasound images, CAT scan images, PET images, X-Ray images), or the like. The treatment information 606 can include available treatments (e.g., based on available medical equipment), recommended treatments, or the like. The marketplace 608 can display medical technology for sale, medical technology location information (e.g., whether nearby or remote), or the like. The clinical support 610 can include recommend test to performed, list of potential diagnosis, diagnosis score (likelihood score), and/or the like. The dashboard can include GUIs, filters (e.g., price filters, rating filters, shipping filters, etc.), navigation menus, or the like and can handle payments to facilitate transactions. The marketplace data can be provided to the patient via a portal, website, or the like and can include, without limitation, available products, prices, shipping information, instructions for use, and/or certification/regulator information. The physician can provide guidance and recommendations based on the available resources that can be sent to the patient or local health-care provider.

In an illustrative embodiment, any of the operations, processes, etc. described herein can be implemented as computer-readable instructions stored on a computer-readable medium (e.g., the memory 206 of FIG. 2). The computer-readable instructions can be executed by a set of processors (e.g., the processors 202 of FIG. 2) of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

Figure 7:
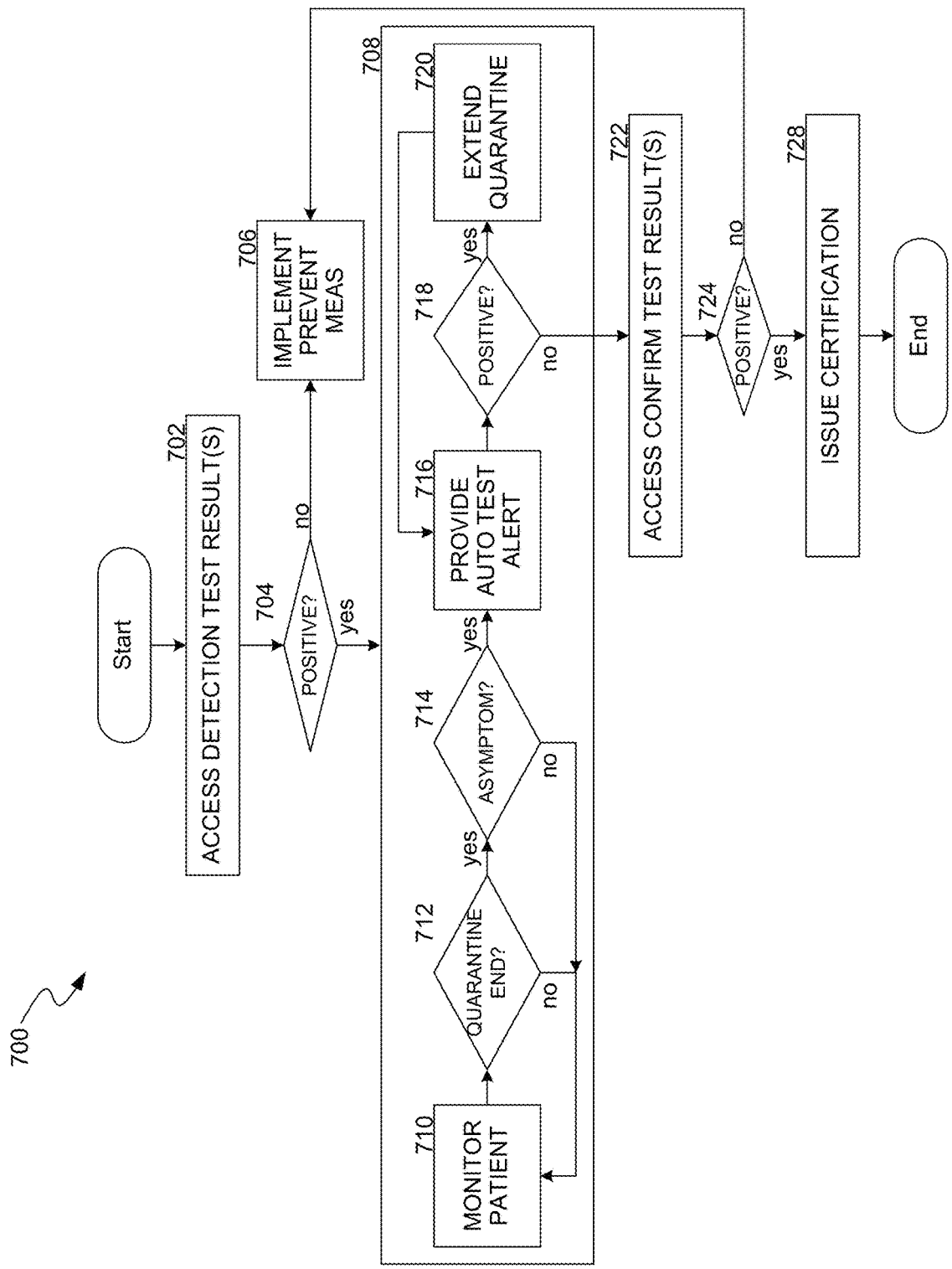
FIG. 7 illustrates a flow diagram for a second example method of operating the virtual telemedicine mechanism in accordance with one or more embodiments of the present technology.

FIG. 7 illustrates a flow diagram for a second example method 700 of operating the virtual telemedicine mechanism in accordance with one or more embodiments of the present technology. The method 700 can be for applying/implementing the real-time concierge service for treating/managing one or more targeted diseases (e.g., COVID-19). The method 700 can be implemented by the system 102 of FIG. 1, the user device 112 of FIG. 1, the electronic concierge network 106 of FIG. 1, the MEC module 208 of FIG. 2, and/or the event module 210 of FIG. 2. The method 700 can correspond to an example implementation of the method 300 of FIG. 3.

The method 700 can correspond to blocks 306-310 of FIG. 3 in responding to and/or managing a targeted disease. The method 700 can start when the user presents symptoms (e.g., fever, cough, shortness of breath) corresponding to the targeted disease (e.g., COVID-19). In some embodiments, the method 700 can start based on input(s) (e.g., reported symptoms and/or method initiation command) provided by the patient-user 510 of FIG. 5 and/or the physician 520 of FIG. 5. Alternatively or additionally, the method 700 can autonomously start (i.e., without initiating input from a user) when data from patient monitor devices (e.g., wearable devices and/or continuous health monitors) match one or more predetermined thresholds or patterns.

At block 702, the virtual telemedicine mechanism can coordinate a detection test and/or access results thereof for the patient user. For COVID-19, the detection test can correspond to an RT-PCR test that directly detects (via, e.g., detecting the presence of viral RNA) the presence of acute SARS-CoV-2 infection. The virtual telemedicine mechanism (e.g., the system 102 of FIG. 1 and/or the electronic concierge network 106 of FIG. 1) can detect updates to the patient health records and access the patient medical history for the test results.

At decision block 704 (corresponding to, e.g., block 308 of FIG. 3), the virtual telemedicine mechanism can determine whether the test results are positive or negative. When the test results are not positive (i.e., the patient user has not been infected with the targeted disease), the concierge service can implement preventative measure, such as illustrated at block 706. For example, the concierge service can inform/remind the user of the preventative guidelines (e.g., social distancing rules, stay-at home recommendations, etc.). The concierge service feature in the virtual telemedicine mechanism can further assist the user with sheltering at home, such as by providing the preventative guidelines (e.g., social distancing rules, stay-at-home recommendations, etc.) and/or by recommending delivery applications and/or stores that deliver to the user location.

When the test results are positive, the concierge service feature of the virtual telemedicine mechanism can implement disease management features, such as illustrated at block 708. The disease management features can include patient monitoring, as illustrated at block 710. The virtual telemedicine mechanism (via, e.g., the user device 112) can monitor the patient current location and/or real-time health indicators. In some embodiments, the concierge service feature can provide location history for contact tracing and/or automatically alert the physician when the patient condition matches a predetermined threshold. The concierge service can further provide the stay-at-home assistance features to the user in quarantine.

At decision block 712, the virtual telemedicine mechanism can determine whether or not the quarantine period has ended. For COVID-19, the recommended quarantine period can be 14 days. Accordingly, the virtual telemedicine mechanism can track the duration of the patient quarantine and compare to the 14-day threshold. When the quarantine has not ended, the virtual telemedicine mechanism can continue to monitor the patient using the user device 112.

When the quarantine ends, the virtual telemedicine mechanism can analyze the patient monitoring data to determine whether or not the patient has become asymptomatic as illustrated at decision block 714. If the patient is not asymptomatic (e.g., if the user continues to have one or more symptoms of the targeted disease) as defined by a set of health monitoring thresholds, the virtual telemedicine mechanism can continue to monitor the patient. If the patient is asymptomatic, the virtual telemedicine mechanism can automatically provide a test alert for re-administering the test as illustrated at block 716. In some embodiments, the virtual telemedicine mechanism can schedule the disease detection test (e.g., the RT-PCR) according to a predetermined scheduling mechanism. At decision block 718, the virtual telemedicine mechanism can determine whether the re-test results are positive or negative (similarly as described above for block 308). When the re-test results are positive (i.e., the patient remains infected by the targeted disease), the virtual telemedicine mechanism can extend the quarantine as illustrated at block 720. The virtual telemedicine mechanism can extend quarantine by a predetermined duration (e.g., 7 more days) and/or according to an input from the physician. The virtual telemedicine mechanism can monitor the patient as described for block 710 until the end of the extended period. The virtual telemedicine mechanism can automatically provide the test alert as illustrated at block 716.

When the re-test results are positive (i.e., the patient remains infected by the targeted disease), the virtual telemedicine mechanism can coordinate a confirmation test and/or access results thereof for the patient user as illustrated at block 722. For COVID-19, the confirmation test can correspond to an antibody/antigen test that indirectly detects the presence of sub-acute SARS-CoV-2 infection. The confirmation test can detect the presence of antibodies and/or antigens to confirm recovery from the targeted disease. At decision block 724, the virtual telemedicine mechanism can determine whether the result of the confirmation test is positive or negative. When the confirmation test result is not positive, the virtual telemedicine mechanism may implement preventative measures as illustrated at block 706. When the confirmation test result is positive, the virtual telemedicine mechanism may issue an immunity certification. The immunity certification may be used as proof for the user recovery. The immunity certification may allow the user to access facilities, services, etc., such as for returning back to work.

As described above, using the current location and the real-time physiological data of the user, the virtual telemedicine mechanism can monitor the patient user while assisting the user to follow related protocols, such as for containment and/or recovery. The actual condition/condition associated with the user may be estimated using the current location and the real-time physiological data, thereby recognizing a meaning or a categorization for the current situation or event associated with the user. The recognized meaning/categorization can be used as a trigger for subsequent services that further assist the user in dealing with the health-conditions. The transformation from the physiological data and location to the context recognition and the subsequent services can lead to changes in the user location and/or the physiological conditions, which can further influence or change the user context. Moreover, the transformation of the physiological data and location to the context recognition and then a trigger/selection mechanism for the subsequent services allows users to access optimized or context-specific healthcare without being limited by language and geography. Further, the virtual telemedicine mechanism can provide contact-less examinations and guide users through rapidly-changing guidelines during ongoing pandemics, thereby reducing the spread of the targeted disease and increasing user recovery rate.

CONCLUSION

The above Detailed Description of examples of the disclosed technology is not intended to be exhaustive or to limit the disclosed technology to the precise form disclosed above. While specific examples for the disclosed technology are described above for illustrative purposes, various equivalent modifications are possible within the scope of the disclosed technology, as those skilled in the relevant art will recognize.

These and other changes can be made to the disclosed technology in light of the above Detailed Description. While the Detailed Description describes certain examples of the disclosed technology as well as the best mode contemplated, the disclosed technology can be practiced in many ways, no matter how detailed the above description appears in text. Details of the system may vary considerably in its specific implementation, while still being encompassed by the technology disclosed herein. As noted above, particular terminology used when describing certain features or aspects of the disclosed technology should not be taken to imply that the terminology is being redefined herein to be restricted to any specific characteristics, features, or aspects of the disclosed technology with which that terminology is associated. Accordingly, the invention is not limited, except as by the appended claims. In general, the terms used in the following claims should not be construed to limit the disclosed technology to the specific examples disclosed in the specification, unless the above Detailed Description section explicitly defines such terms.

Although certain aspects of the invention are presented below in certain claim forms, the applicant contemplates the various aspects of the invention in any number of claim forms. Accordingly, the applicant reserves the right to pursue additional claims after filing this application to pursue such additional claim forms, in either this application or in a continuing application.

What is claimed is:

1. A non-transitory computer-readable medium having instructions thereon that, when executed by a processor, perform a method of operating a virtual telemedicine system, the method comprising:
   determining a current location representative of a user, wherein determining the current location includes interacting with a mobile device associated with the user;
   receiving health-related data corresponding to a real-time physiological condition of the user;
   identifying a health-related context based on the health-related data, wherein the health-related context represents an event that is associated with the physiological condition of the user and requires a medical review;
   determining whether the health-related context is associated with a geographic limitation related to the current location of the user; and
   generating a concierge output based on the determined geographic limitation, wherein the concierge output is for assisting the user with receiving the medical review for the health-related context based on or in accordance with the geographic limitation.

2. The non-transitory computer-readable medium of claim 1, wherein:
   determining whether the health-related context is associated with the geographic limitation includes determining that the event is estimated to be an emergency event;
   generating the concierge output includes providing a healthcare facility location to the user in response to estimating the emergency event; and
   the instructions corresponding to the method that further comprises:
   identifying the healthcare facility corresponding to a travel time less than a predetermined response limit associated with the estimated emergency event.

3. The non-transitory computer-readable medium of claim 2, wherein:
   the health-related data represents measurements and/or sensor outputs from a wearable device, a continuous health monitor, a user mobile device, or a combination thereof; and
   generating the concierge output includes providing the health-related data to the selected healthcare facility.

4. The non-transitory computer-readable medium of claim 1, wherein:
   determining whether the health-related context is associated with the geographic limitation includes determining that the health-related context is applicable for virtual review; and
   generating the concierge output includes facilitating a real-time telecommunication session connecting the user to a remote healthcare provider in response to the determination.

5. The non-transitory computer-readable medium of claim 4, wherein the real-time telecommunication session is a telemedicine session for providing virtual healthcare services to the user.

6. The non-transitory computer-readable medium of claim 1, wherein:
   identifying the health-related context includes determining that the health-related data corresponds to one or more symptoms indicative of an infectious carrier;
   determining whether health-related context is associated with the geographic limitation includes determining a quarantine status based on accessing a test result for detecting the infectious carrier; and
   generating the concierge output includes generating health monitor outputs based on monitoring the user over a quarantine period when the test result indicates the infectious carrier.

7. The non-transitory computer-readable medium of claim 6, wherein generating the concierge output includes:
   determining that the user is asymptomatic based on the health monitor outputs; and
   automatically generating a test alert when the user is asymptomatic, wherein the test alert is for re-taking the detection test.

8. The non-transitory computer-readable medium of claim 7, wherein generating the concierge output includes:
   accessing a confirmation test result; and
   issuing a recovery certification when the confirmation test result indicates presence of antibodies.

9. The non-transitory computer-readable medium of claim 8, wherein generating the concierge output includes communicating the recovery certification to one or more remote devices for certifying a recovery condition of the user to remote device users.

10. A system comprising:
    a communication circuit configured to exchange data with one or more remote devices including at least a mobile device;
    at least one processor coupled to the communication circuit;
    at least one memory operably coupled to the processor and having stored thereon instructions executable by the processor to cause the processor to:
    determine a real-time location of a user based on interactions with the mobile device associated with the user;
    receive data corresponding to a real-time physiological condition of the user;
    identify a health-related context based on the received data, wherein the health-related context represents an event that is associated with the physiological condition of the user and requires a medical review;
    determine whether the health-related context is associated with a geographic limitation related to the current location of the user; and
    generate a concierge output based on the determined geographic limitation, wherein the concierge output is for assisting the user with receiving the medical review for the health-related context in accordance with the geographic limitation.

11. The system of claim 10, wherein:
    the communication circuit is communicatively coupled to a wearable device, a continuous health monitor, a mobile computing device, or a combination thereof; and
    the health-related data represents measurements and/or sensor outputs from the wearable device, the continuous health monitor, the mobile computing device, or a combination thereof.

12. The system of claim 10, wherein the instructions further cause the processor to:
    determine that the health-related context is an emergency event based on the health-related data;
    identifying a healthcare facility that corresponds to a travel time less than a predetermined response limit associated with the estimated emergency event; and
    communicate a location of the selected healthcare facility to the user.

13. The system of claim 12, wherein the instructions further cause the processor to communicate the health-related data to the selected healthcare facility.

14. The system of claim 10, wherein the instructions further cause the processor to:
   determine that the health-related context is applicable for remote review; and
   in response to the remote applicability determination, provide the concierge output by facilitating a real-time telecommunication session connecting the user to a remote healthcare provider.

15. The system of claim 14, wherein:
   the identified health-related context includes a determination that the health-related data corresponds to one or more symptoms indicative of an infectious disease;
   the association between the health-related context and the geographic limitation includes determining a quarantine status based on accessing a detection test result for determining whether the user has been infected with the disease; and
   the concierge output includes autonomously obtained outputs from a health monitor associated with the user over a quarantine period when the detection test result indicates that the user has been infected with the disease.

16. The system of claim 15, wherein the instructions further cause the processor to:
   determine that the user is asymptomatic based on the health monitor outputs;
   access a confirmation test result following the asymptomatic determination; and
   generate the concierge output including a recovery certification when the confirmation test result indicates presence of antibodies for the disease within a body of the user.

17. A method of operating a virtual telemedicine system, the method comprising:
   determining a current location representative of a user, wherein determining the current location includes interacting with a mobile user device;
   receiving data corresponding to a real-time physiological condition of the user;
   identifying a health-related context based on the current location and the received data, wherein the health-related context represents the physiological condition of the user, requires a medical review, and is associated with a geographic limitation related to the current location of the user; and
   generating a concierge output based on the health-related context, wherein the concierge output is for assisting the user with receiving the medical review for the health-related context based on or in accordance with the geographic limitation.

18. The method of claim 17, further comprising:
   deriving the geographic limitation for search parameters based on the health-related context; and
   the concierge output includes one or more search results that satisfy the geographic limitation.

19. The method of claim 17, further comprising:
   initiating, based on the concierge output, a real-time video conference for connecting the user with a physician at a remote location different from the current location.

20. The method of claim 17, wherein the concierge output includes a set of features when the health-related context includes a determination that the user tested positive for an infectious disease, the set of features including:
   identifying a quarantine duration;
   monitoring one or more sensor outputs during at least a portion of the quarantine duration, wherein the one or more sensor outputs represent corresponding physiological conditions of the user;
   determining that the user is asymptomatic based on the monitored sensor outputs;
   accessing a confirmation test result; and
   generating a recovery certification when the confirmation test result indicates presence of antibodies for the disease within a body of the user.

* * * * *